United States Patent
Novik

(10) Patent No.: US 10,638,925 B2
(45) Date of Patent: May 5, 2020

(54) DETERMINING VISION RELATED PHYSICAL CONDITIONS FROM CROSS-PARAMETER VISION TESTS

(71) Applicant: EYEKON E.R.D. LTD., Ramat Gan (IL)

(72) Inventor: Shai Novik, Ramat Hasharon (IL)

(73) Assignee: EYEKON E.R.D. LTD., Ramat Gan (IL)

( * ) Notice: Subject to any disclaimer, the term of this patent is extended or adjusted under 35 U.S.C. 154(b) by 56 days.

(21) Appl. No.: 15/527,014

(22) PCT Filed: Nov. 26, 2015

(86) PCT No.: PCT/IL2015/051152
§ 371 (c)(1),
(2) Date: May 16, 2017

(87) PCT Pub. No.: WO2016/084086
PCT Pub. Date: Jun. 2, 2016

(65) Prior Publication Data
US 2017/0360293 A1    Dec. 21, 2017

Related U.S. Application Data

(60) Provisional application No. 62/155,182, filed on Apr. 30, 2015, provisional application No. 61/996,967, filed on Nov. 26, 2014.

(51) Int. Cl.
*G02B 3/02* (2006.01)
*G02B 3/00* (2006.01)
(Continued)

(52) U.S. Cl.
CPC .............. *A61B 3/022* (2013.01); *A61B 3/036* (2013.01); *A61B 5/168* (2013.01); *G09B 21/008* (2013.01); *A61B 3/06* (2013.01)

(58) Field of Classification Search
CPC ....... A61B 3/0025; A61B 3/102; A61B 3/028; A61B 3/113; A61B 3/0033; A61B 3/0041;
(Continued)

(56) References Cited

U.S. PATENT DOCUMENTS

2003/0147048 A1 * 8/2003 Mihashi ................. A61B 3/022
351/211
2009/0270717 A1 10/2009 Newman
(Continued)

FOREIGN PATENT DOCUMENTS

WO    WO 2013/170091 A1    11/2013

OTHER PUBLICATIONS

International Search Report for PCT Application No. PCT/IL2015/051152 dated Mar. 11, 2016.

*Primary Examiner* — Brandi N Thomas
(74) *Attorney, Agent, or Firm* — Mark Cohen; Pearl Cohen; Zedek Latzer Baratz

(57) ABSTRACT

A method and system for determining visual related physical conditions of a user of a display device, determined from the user's responses to a selection of visual-tasks. A dataset is provided for correlating the user's responses with the corresponding scores, so that by measuring the degree of correlation between the user's scores and a predetermined combination of the corresponding scores, the user's visual physical condition can be determined. A system is also provided, including a user device as well as a remote server for providing visual acuity and related testing to detect certain vision deficiencies and visual related physical conditions. In addition, a user device application is provided.

14 Claims, 13 Drawing Sheets

(51) Int. Cl.
   *A61B 3/02*       (2006.01)
   *A61B 3/036*      (2006.01)
   *A61B 5/16*       (2006.01)
   *G09B 21/00*      (2006.01)
   *A61B 3/06*       (2006.01)

(58) Field of Classification Search
   CPC ....... A61B 3/0091; A61B 3/085; A61B 3/117;
            A61B 3/18; A61B 5/0066; A61B 5/0073;
            A61B 8/10; A61B 8/5223; A61B 3/00;
            A61B 3/101; A61B 3/13; A61B 3/14;
            G02B 2027/011; G02B 2027/0138; G02B
            2027/014; G02B 2027/0178; G02B 27/01;
            G02B 27/0172; G02B 7/28
   USPC ........ 351/200, 205, 206, 209–211, 221, 222,
                                         351/239, 243–246
   See application file for complete search history.

(56) References Cited

U.S. PATENT DOCUMENTS

2010/0292999 A1* 11/2010 Verma ................... A61B 3/005
                                                              705/2
2011/0063571 A1   3/2011 Duffy

* cited by examiner

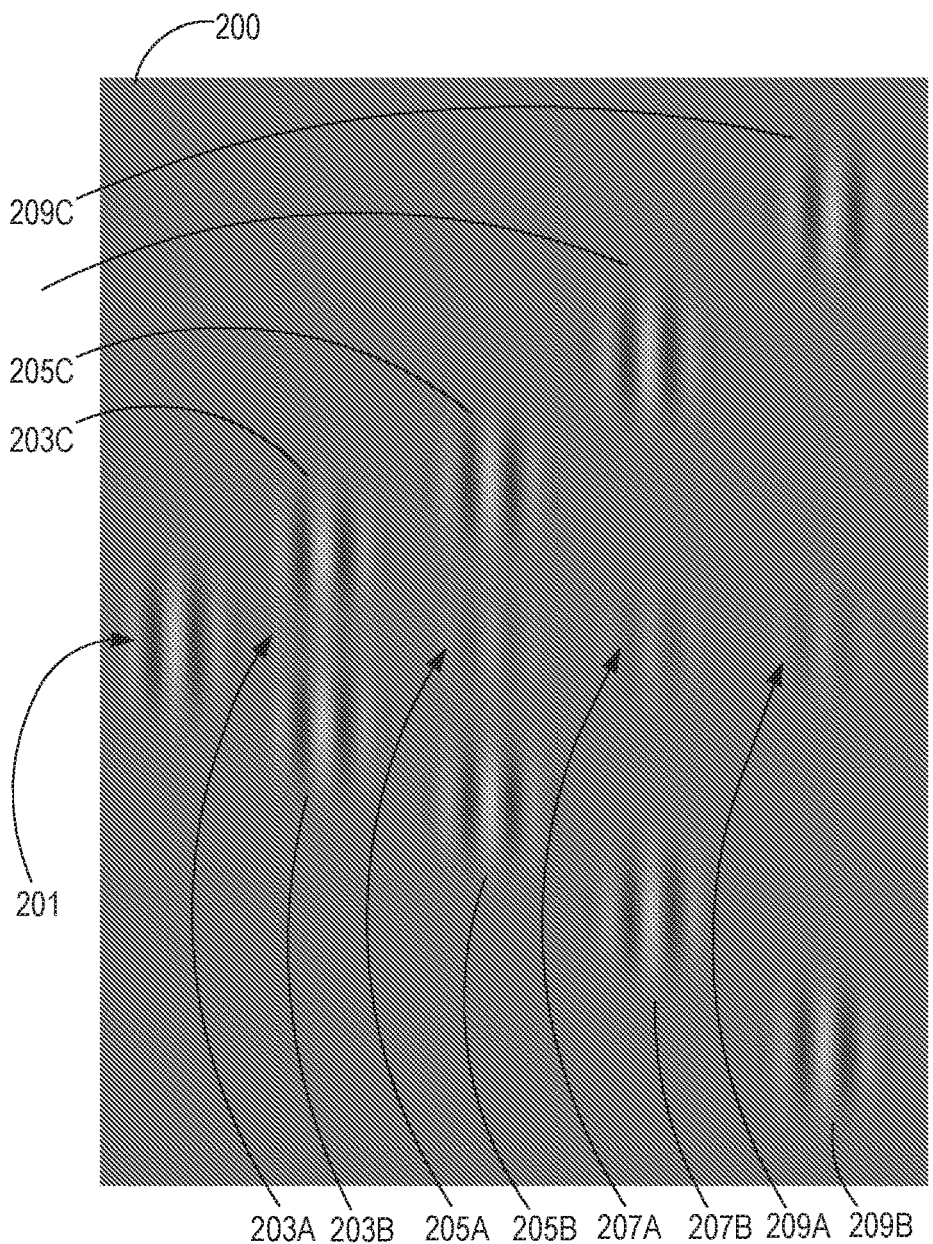
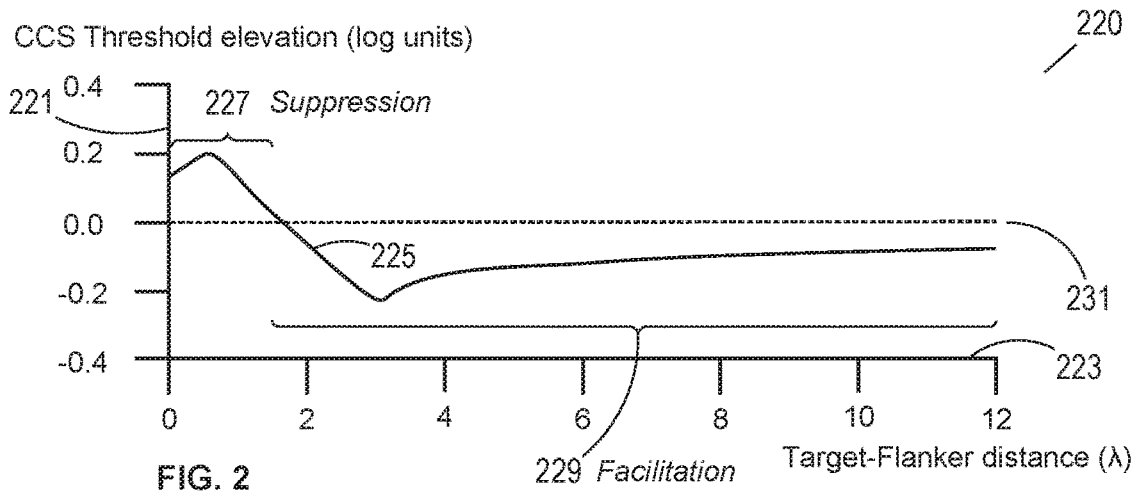
FIG. 2

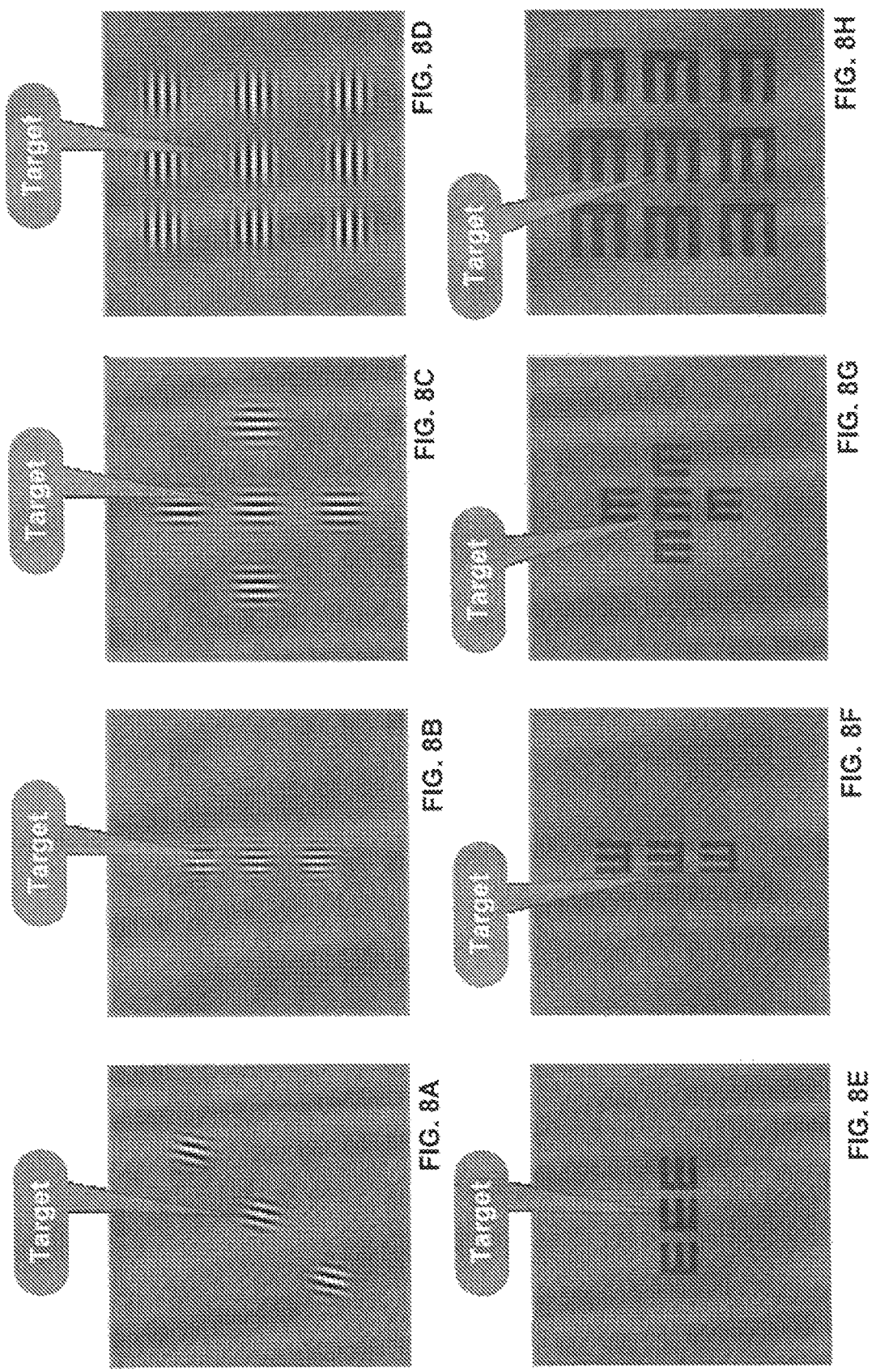

DETERMINING VISION RELATED PHYSICAL CONDITIONS FROM CROSS-PARAMETER VISION TESTS

CROSS-REFERENCE TO RELATED APPLICATIONS

This application is a National Phase Application of PCT International Application No. PCT/IL2015/051152, International Filing Date Nov. 26, 2015, claiming priority of U.S. Patent Application No. 61/996,967, filed Nov. 26, 2014, and U.S. Patent Application No. 62/155,182, filed Apr. 30, 2015, which are hereby incorporated by reference in their entirety.

BACKGROUND

Visual acuity (VA) is the most commonly-used measure of human visual function, and is considered the standard measure of visual function in clinical settings. Standard tests of VA measure the ability to identify black symbols on a white background at a standardized distance as a function of the size of the symbols, such as with one of the familiar eye charts (e.g., Snellen, Bailey-Lovie, Tumbling E, Landolt C, and so forth) at a standardized distance of approximately 6 meters or 20 feet. A person with standard (normal) VA can recognize a letter or a symbol that subtends an angle of 5 arc minutes. The block letter E, for example, has three horizontal black strokes plus two interspersed horizontal white spaces of comparable thickness, meaning that normal human visual resolution is nominally one (1) arc minute. For angular values of this magnitude, the angle subtended by an object is approximately inversely proportional to distance.

Clinically, a level of VA specified as 6/6 (meters) or 20/20 (feet) is considered good normal vision. An alternative clinical measure of VA is expressed as the Logarithm of the Minimum Angle of Resolution (LogMAR), where 6/6 or 20/20 has a LogMAR VA measure of 0.0; 6/60 or 20/200 has a LogMAR VA measure of 1.0; and 6/3 or 20/10 has a LogMAR VA measure of −0.3). Measures of VA herein also include a measure of the ability to see a given object size at a given duration of exposure and/or at a given contrast level.

There are drawbacks to directly measuring VA as described above. Typically VA must be measured via an eye chart with the aid of clinician, who instructs the subject to read a specific line of the eye chart and then evaluates the subject's response. In addition, there are cases for which the VA falls within the range of normal vision even in the presence of severe visual problems and eye diseases, such as glaucoma or early retinopathy.

Thus, it would be useful and desirable to have alternative or complementary visual testing methods for clinical and research use, which achieve a high degree of correlation with the eye chart, but which can be administered without the need for a clinician, and which have the potential to detect visual pathologies. This goal is met by embodiments of the present invention.

Attention-Deficit Hyperactivity Disorder (ADHD) is a common neurobehavioral disorder that impairs the quality of life in both children and adults. The main symptoms include inattentiveness, hyperactivity and impulsivity. ADHD is usually diagnosed in childhood and often lasts into adulthood. Currently there is no simple objective diagnostic or screening test for ADHD. ADHD is diagnosed by clinicians in a several step process, using highly subjective tools, such as questionnaires, sometimes supported by computerized tests (T.O.V.A., MOXO). In children in particular, the diagnosis is confounded by parent's subjective input and child's general intelligence level. Accordingly there is a further need for an accessible screening tool that can assist adults with ADHD symptoms and parents to decide whether to seek clinical assessment.

SUMMARY

Static vs. Dynamic Images

Embodiments of the present invention rely on static images. The term "static", in the context of images, herein denotes an image that does not perceptibly change in orientation and/or position as time progresses. A static image, however, may change perceptibly in brightness, contrast, and/or color, as time progresses. In particular, a static image may be made visible and/or non-visible as time progresses.

In distinction, the term "dynamic", in the context of images, herein denotes an image that perceptibly changes in orientation and/or position as time progresses (e.g., a moving or non-stationary image). In the case of orientation, a change of orientation is understood to include a rotation of a three-dimensional object (virtual or real) which is projected onto a two-dimensional surface, a non-limiting example of which is a two-dimensional image of a spinning globe. A dynamic image need not be constantly changing in orientation and/or position: an image may remain perceptibly unchanging for a time and may still be considered a "dynamic" image, provided that the image is capable of being perceptibly changed in orientation and/or position, and be readily perceived as moving by an observer.

The terms "static" and "dynamic", as used herein, are mutually-exclusive, in that static images are non-dynamic, and dynamic images are non-static. In an embodiment of the invention an estimation of contrast sensitivity (CS) is made from static images; in another embodiment of the invention, an estimation of CS is made from dynamic images.

Contrast Sensitivity

"Contrast sensitivity (CS)", as used herein, denotes the ability to discriminate between shades of gray. CS is one of the main determinants of how well people see. It is assumed that there exists a contrast sensitivity function (CSF) that describes the combined response of the brain cells (neurons) in the visual area which have been selectively tuned for location, orientation, and spatial frequency, and which constitute the fundamental units of analysis. Thus, CSF describes the output of the early stage that serves as the building blocks for the succeeding steps of visual processing. Therefore, the fidelity of this output may determine how well higher visual areas process the information and hence their output including their feedback to the lower visual areas.

CS is known to be sensitive to subtle decreases in visual function caused by various eye diseases and pathologies, such as corneal edema, keratoconus, early rejection of corneal grafts, the aftermath of refractive surgery, diabetic retinopathy, glaucoma, diabetes without retinopathy, and others. The ability to perform daily life functions is correlated with CS. Reduced CS can be detected in individuals having only a slight loss in VA. Therefore, CS testing is relevant for assessing visual function and visual deficiencies.

CS testing is also useful in predicting the performance of routine daily activities of both patients and healthy subjects. For example, CS is the most important parameter for predicting improvement in driving performance after binocular cataract surgery, as well as in other driving-related tasks. CS also predicts how well people can see natural targets according to their age. Importantly, CS is superior to standard VA in predicting the performance in air-ground target detection under various visibility conditions, both in simulations and in the field. CS is significantly higher in aircrew subjects as compared with non-aircrew subjects, and significantly higher CS values at spatial frequencies of 3, 6, and 11.4 cycles per degree (cpd) are typically measured in combat fighter pilots when compared with non-aircrew subjects. CS, but not VA, is related to short detection times in combat field-related recognition tasks. Overall, measuring CS typically provides more useful information than does measuring VA.

There have been attempts to diagnose certain visual dysfunctions using the CSF, by characterizing which spatial frequencies are abnormal. However, the variability of the results is large and the specificity of the diagnosis therefrom is unsatisfactory. In addition, these tests require the aid of a clinician and cannot be performed as a remote self-evaluation. Thus, even though CSF analysis may flag visual deficiencies it still cannot reliably distinguish between different eye diseases, and, more importantly, the results may be obscured by reduced VA. Moreover, despite good VA as measured via an eye chart, there may be significant abnormalities in CSF. The scores of CSF and VA are correlated, and therefore reduced VA in cases involving uncorrected myopia, presbyopia amblyopia can complicate the evaluation. Thus, bad CSF performance may result from uncorrected vision. For example, myopes who undergo CSF testing without corrective lenses for distance may fail a CSF test at distance; similarly, people with presbyopia (aging eye) who undergo a CSF test from near without reading glasses will likewise fail the CSF test.

Complex Contrast Sensitivity and Modulation

The term "complex contrast sensitivity (CCS)", as used herein, denotes CS test or VA test, which present a central target pattern with (or in the presence of) flanking patterns, as illustrated in FIG. 1, FIG. 2 and FIG. 8A-8H, disclosed herein as non-limiting examples. Accordingly, complex visual acuity (CVA) is a specific case of CCS.

The term "modulation", as used herein, denotes modifying a CS pattern to include flanking patterns, as described herein for measuring CCS.

Various embodiments of the present invention provide methods of determining VA via remotely self-administered visual testing of CCS and a complex contrast sensitivity function (CCSF). Related embodiments provide reliable diagnostic CCSF tools for various visual disorders.

Additional embodiments of the present invention provide tests using CCSF with specific time durations and spatial frequencies anticipated from VA tests, to detect any deviations from the outcome predicted by the VA testing. In a related embodiment, discrepancies between the VA and CCSF are analyzed via Gabor patches combined with spatial interactions. Because different visual deficiencies affect different spatial frequencies, the deviations can thus be associated with specific visual deficiencies. The testing of CCS can be used to provide additional information about visual deficiencies that are not detectable by standard VA, such as but not limited to diagnosis of ADHD both for children and adults, attention deficit, hyperactivity disorder and dyslexia, as will be demonstrated in the following.

Embodiments of the present invention allow remote automated testing to determine VA without the use of eye charts and the aid of clinician. In a non-limiting example, an embodiment of the invention provides a means for an individual user with a smartphone to use the smartphone to automatically self-administer a VA test at virtually any location. Another embodiment of the invention provides for determining VA of a user whose vision is not optically corrected. This embodiment allows a user, who normally sees with the aid of corrective lenses, to test his or her VA while not wearing the corrective lenses.

Complex Contrast Sensitivity and Modulation

VA can be measured by means of single target or target that is embedded between other targets. VA elevation by testing CCS is measured as the differences or the ratio between at least two measures of VA, that at least one of them is different by target-flanker separations, presentation time and any other physical attributes. Different conditions exhibit different VA elevation. For example ADHD subjects may have same VA as non-ADHD control subjects, but can exhibit different threshold elevation depends on physical attributes such as presentation time, target-flanker separation and the subject's age.

Diagnosis of Medical Conditions Affecting Visual Function

The term "vision related physical condition", as used herein, refers to any condition that has an impact on vision performance. Examples include, but are not limited to: amblyopia, retinopathy, glaucoma, attention deficit disorder (ADD), Attention-Deficit Hyperactivity Disorder (ADHD), and dyslexia.

The term "visual task", as used herein, refers to an image or a set of images that is/are presented to a user and promotes the user to respond. Non-limiting examples for such a promote include: identify a target-image, identify a state or position or orientation of a target-image, specifically manipulate a target-image, follow a target-image/s, count target-images, and any task that prompts a user's response. According to some embodiments of the present disclosure, the target-image (static or dynamic) can be presented with at least one of: distractor-images (static or dynamic), background, backward masking.

Certain embodiments of the present invention provide tests for differential diagnosis of medical conditions affecting visual function. In differential diagnosis, several possible diagnoses are compared and contrasted, involving the correlation of various observations and test results followed by the recognition and differentiation of patterns.

Differences between conditions are typically based on data collected from groups of subjects, and decisions about specific condition are then made by comparing different groups according to statistical measures. Unfortunately, this does not adequately address the case where a decision needs to be made according to a single test. In this case, the true positive and false positive rates reveal the sensitivity and specificity of the test. High sensitivity and high specificity increase the probability of correct diagnosis. Typically, however, there is a significant overlap between true positive and false positive, thereby impacting the ability to make a correct decision from a single test. That is, the difference between groups often relies on statistical factors, making it difficult to decide which group a subject is in without further testing. In particular, it is known in the art that the contrast sensitivity of patients with glaucoma or retinopathy is different from the contrast sensitivity of normal-vision control groups. However, the difference is between the group averages, and the specificity is not high, especially when testing non-severe conditions, so that there is a large overlap.

Specific embodiments of the present invention provide automated diagnosis of certain vision deficiencies to overcome the above restrictions, by combining several different tests, such as: standard VA compared with CVA; CS testing coupled with CCS; and modulation of CS thresholds and modulations of VA using static images; as detailed herein. Testing according to these embodiments can accumulate additional data, and via lookup in the data base provided by other embodiments of the invention, it is possible to attain high probability levels for diagnosis of conditions including, but not limited to: glaucoma, retinopathy, amblyopia, presbyopia, ADHD, and dyslexia. In related embodiments, differentiation is based on a function of affected spatial frequencies.

The advantages provided by embodiments of the present invention can be seen in a non-limiting example involving diagnosis of attention deficit/hyperactivity disorder (ADHD), a common behavioral disorder with a genetic component. Diagnosis of ADHD is typically performed by clinicians using subjective tools and questionnaires, or by computerized continuous performance tests (CPT) with uncertain reliability as screening diagnostic tools. Using prior art methods, it is often difficult to reach objective conclusion due to high variance, false positives, and the inability to perform remote self-testing. To overcome this restriction, an embodiment of the present invention provides remote, easy to use self-testing to diagnose ADHD.

The known measuring tools in the art include: Visual Acuity (VA) which measures the minimal spatial resolution, where near VA is measured using reading charts, such as ETDRS, tumbling E-test and crowding charts which display impaired target recognition due to the presence of neighboring distractor elements; a phenomenon that is related to one's reading ability. Various studies demonstrated the usefulness of VA under crowded conditions for measuring visual performance, both in adults and children.

According to embodiments of the invention, a paradigm is disclosed based on spatial and temporal visual stimulations which are used to identify ADHD symptoms, both in young and adult participants, as also demonstrated in FIGS. 12A-12D.

Therefore, an embodiment of the present invention discloses a new method for presenting images to a user, for determining at least one vision related physical condition, the method comprising processor implemented steps of:
displaying two or more visual-tasks selected from the group essentially consisting of:
CS target pattern,
CCS,
backward masking with any of: CS target pattern, CS central target pattern with flanking patterns, tumbling target symbol, and the tumbling central target symbol between plurality of flanking symbols, and and any combination thereof;
measuring responses of the user to the displayed visual-tasks;
associating the user's responses with a dataset of expected results, respective to the displayed the visual-tasks; and
retrieving measurements of least one vision related physical condition, corresponding to a predetermined combination of the degree of correlation between the user's responses and the associated expected results.

According to another embodiment, the present invention discloses a new method for presenting images to a user, for determining at least one vision related physical condition, the method comprising processor implemented steps of:
displaying two or more visual-tasks to a user, wherein at least one of the visual-tasks is configured for complex contrast sensitivity (CCS) examination, via a display device;
measuring responses of the user to the displayed visual-tasks, via a input interface;
associating the user's responses with a dataset of expected results, respective to the displayed the visual-tasks; and
retrieving measurements of least one vision related physical condition, corresponding to a predetermined combination of the degree of correlation between the user's responses and the associated expected results According to another embodiment, the present invention discloses a new device configured to determine at least one vision related physical condition of a user, the device comprising:
at least one display-device, configured to display at least two visual-tasks to the user, wherein at least one of the visual-tasks is configured to examine complex contrast sensitivity (CCS);
at least one input-device, configured to collect and interpret, user's response/s to the displayed visual-tasks; and
at least one processor configured to:
associate the user's responses with a dataset of expected results, respective to the displayed the visual-tasks; and
retrieve measurements of least one vision related physical condition, corresponding to a predetermined combination of the degree of correlation between the user's responses and the associated expected results.

According to another embodiment, the present invention discloses a new transitory or non-transitory computer readable medium (CRM) comprising executable code instructions, which instructions when executed by a data processor cause the data processor to perform a method for presenting images to a user, for determining at least one vision related physical condition, the method comprising steps of:
displaying two or more visual-tasks to a user, wherein at least one of the visual-tasks is complex contrast sensitivity (CCS) examination;
measuring responses of the user to the displayed visual-tasks;
associating the user's responses with a dataset of expected results, respective to the displayed the visual-tasks; and
retrieving measurements of least one vision related physical condition, corresponding to a predetermined combination of the degree of correlation between the user's responses and the associated expected results.

BRIEF DESCRIPTION OF THE DRAWINGS

The subject matter disclosed may best be understood by reference to the following detailed description when read with the accompanying drawings in which:

FIG. 2 conceptually illustrates the effect on visibility of Gabor patches of target patterns with vertical flanking patterns at different separations;

FIGS. 6A and 6B conceptually illustrate a visual task of tumbling central target symbol between plurality of flanking symbols, presenting two different predetermined spacing distance there-between;

FIGS. 8A, 8B, 8C, 8D, 8E, 8F, 8G, and 8H conceptually illustrate Gabor patch target patterns with flanking patterns at various arrangements (FIGS. 8A-8D) and tumbling E charts with flanking patterns at various arrangements (FIGS. 8E-8H);

Figure 1:
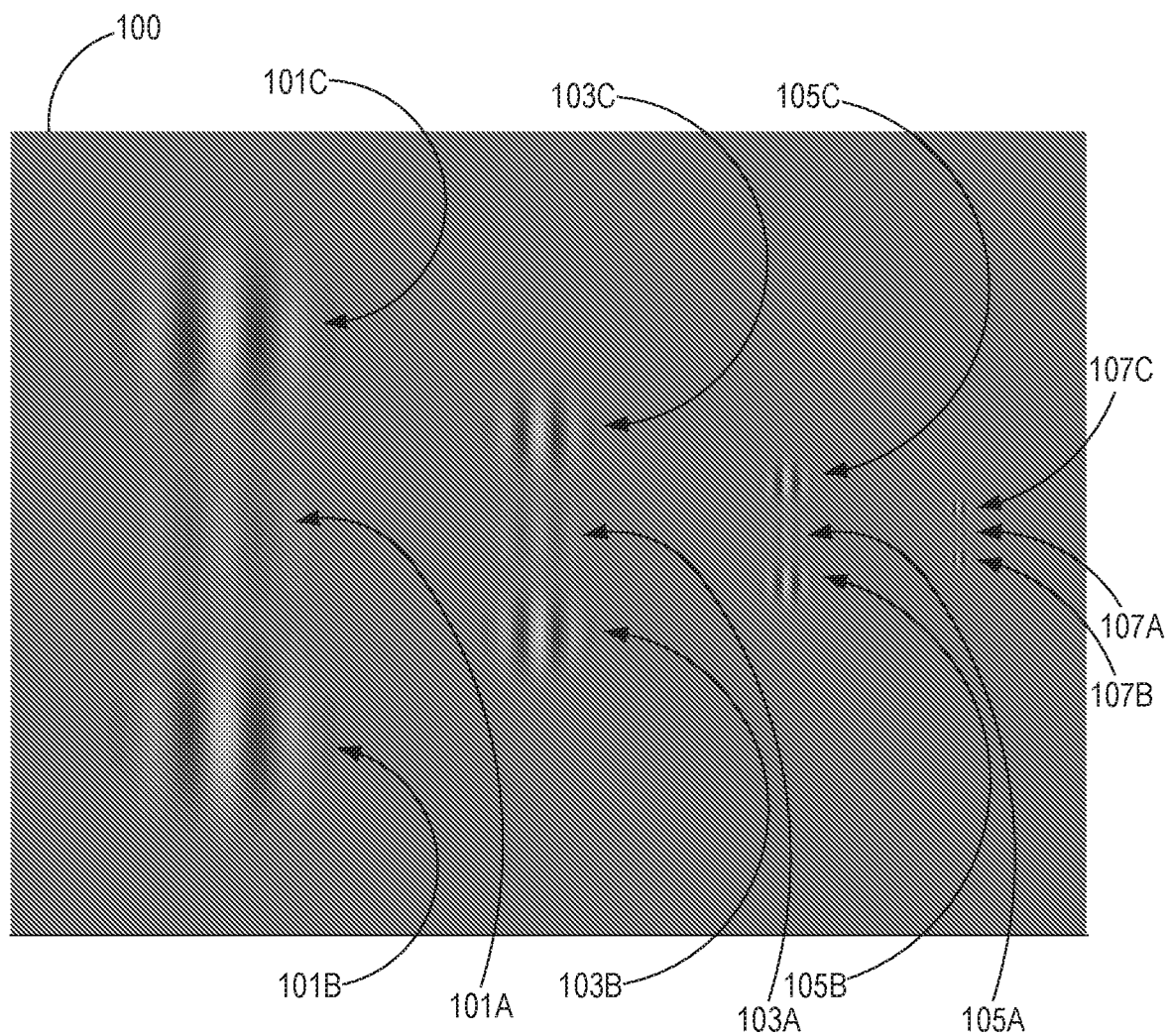
FIG. 1 conceptually illustrates Gabor patch target patterns with vertical flanking patterns at various spatial wavelengths.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

It is known that the visibility of a local target (E letter) deteriorate when it is presented between other letters (crowding), especially when the target-flanker spatial separations are small. The difference between the VA of target alone and that of a target with flanker, in conjunction with the measure of the usual VA, is defined as CVA. CVA depends on several parameters, such as the distance between target and flanking letters, presentation time, contrast and age of the examined user and the condition of the examined user. For example, the testing results of people with amblyopia (lazy eye, mainly strbismic amblyopia) are highly affected by the crowding letters specifically for their amblyopic eye, but not for their healthy eye, and the affect is independent of age. However, since their VA is reduced, their CVA may be moderate as well.

On the other hand, people with ADHD exhibit high CVA when tested with both eyes, and this effect is different with the different age of the examined users, namely age dependent. Specifically, the VA of a single letter (with no flanking letters) may be normal for adults but not for visually healthy children, and the VA may increase highly when testing with flanking letters (CVA), also depend of age. Accordingly, our algorithm and database may distinguish between these conditions solely based on calculating the CVA. In some cases, the algorithm may continue testing the CCS to reach higher degree of certainty; examples are shown in the following.

It is known that the visibility of a local target (Gabor patch) improves when it is presented between two collinear masks, especially when the target-mask spatial separations are small. Collinear masks (denoted as "flanking patterns" or "flankers") tend to affect neural activity at locations corresponding to the target, such that there is increased neural activity in the neural network that processes the stimuli at locations not directly stimulated by the input, but rather by lateral interactions within the neural network. In normal vision, the visibility of the target is influenced by the presence of nearby flankers.

FIG. 1 illustrates this effect for various wavelengths ($\lambda$) in a visual area 100 having a target pattern 101A with a lower flanker 101B and an upper flanker 101C, a target pattern 103A with a lower flanker 103B and an upper flanker 103C, a target pattern 105A with a lower flanker 105B and an upper flanker 105C, and a target pattern 107A with a lower flanker 107B and an upper flanker 107C.

FIG. 2 illustrates the effect that target-flanker distance has on the perceived contrast for a target of a given wavelength $\lambda$, and the resulting effect on VA. Target-flanker distance is measured from target pattern center to flanker pattern center. A visual area 200 has a target pattern 201 whose lower flanker and upper flanker have zero distance from target pattern 201, i.e., where there is complete overlapping of the flankers with target pattern 201. A target pattern 203A, however, is only partially overlapped by a lower flanker 203B and an upper flanker 203C, where the target-flanker distance is of the order of $2\lambda$. Also shown are: target patterns 205A, 207A, and 209A, with lower flankers 205B, 207B and 209B, respectively, and with upper flankers 205C, 207C, and 209C, respectively, shown with increasingly larger target-flanker distances which approximately correspond to the calibrations of a horizontal axis 223 showing target-flanker distance in a plot 220. Plot 220 shows the elevation (both suppression and facilitation) of the CCS threshold regarding perception of the target pattern as a function 225 of target-flanker distance. Threshold elevation is indicated relative to no elevation as shown by a dashed line 231 at a value of 0.0, where threshold elevation is measured in log units on a vertical axis 221. Dashed line 231 indicates the CS threshold without modulation, i.e., without flanking patterns. Curve 225 represents the modulation of CS as a function of flanker distance.

For overlapping target and flanker patterns the CCS threshold is suppressed, as indicated for a suppression region 227 (increasing log unit values). For non-overlapping flanker separation of $2\lambda$ or more, the threshold perception is facilitated, reaching a maximum at $3\lambda$ and decreasing thereafter, as indicated for a facilitation region 229. This effect of sensitivity modulation is found independent of the spatial frequency of the target and flankers.

The advantage of measuring CS thresholds as a function of modulated contrast, via changed target-flanker distance, is that it makes it possible to independently assess the neural sensitivity component of the VA and thereby detect certain visual deficiencies such as amblyopia. However, individual measurements of CS and VA should also be retained to prevent losing important information for other clinical purposes.

An embodiment of the present invention provides a dataset that correlates CCS (CS of a target with flankers) with VA, wherein the dataset entries are based on combined measurements of CCS, CVA and VA. According to a related embodiment, this dataset can be used to determine VA based on a measurement of CCS. In another related embodiment, the calculation uses various spatial frequencies, as shown in FIG. 1, to increase the reliability of the measure.

In an embodiment of the invention, this technique is used in stand-alone measurements. In a related embodiment it is used in combination with VA measurements to remotely assess user visual deficiencies. In certain embodiments, the VA is found by using only one spatial frequency. In other embodiments, however, using specific spatial frequencies provides specific information regarding particular visual deficiencies. In a non-limiting example, a user with amblyopia may have normal VA at lower spatial frequencies, but reduced VA at higher spatial frequencies. Likewise, a user with retinopathy will have a pronounced reduction in VA at specific high spatial frequencies, whereas a user with glaucoma will have uniformly reduced VA at all spatial frequencies.

Figure 3:
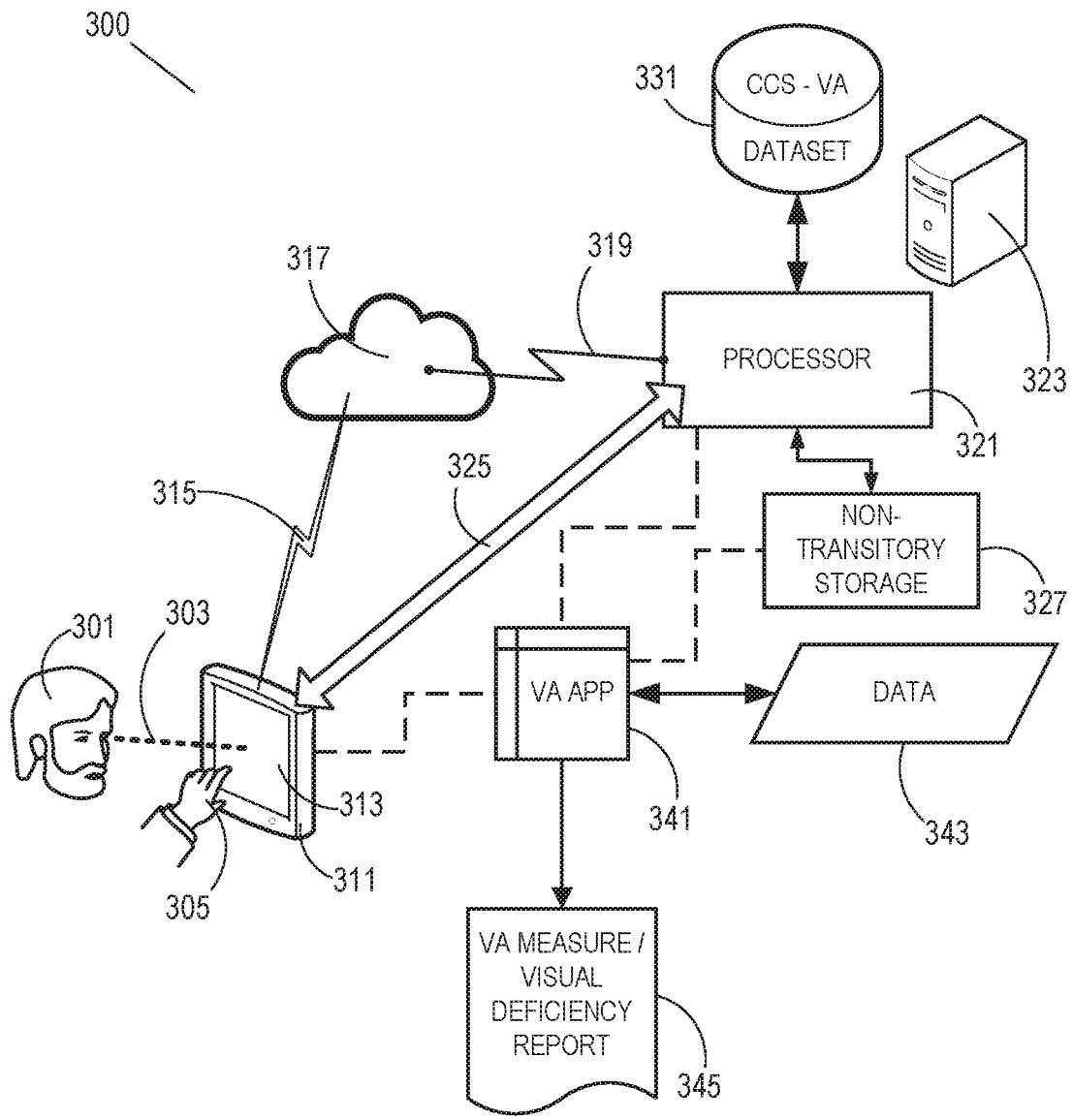
FIG. 3 conceptually illustrates a system for determining at least one vision related physical condition from at least two visual tasks, according to an embodiment of the present invention.

FIG. 3 conceptually illustrates a system 300 for determining vision related physical condition from a selected number of different visual tasks compared and correlated to a predetermined combination of threshold measurements, according to an embodiment of the present invention.

A user 301 has a device 311 with a display screen 313 upon which target visual patterns, such as illustrated in FIG. 1, FIG. 2, FIGS. 5A-5C FIGS. 6A-6B and FIGS. 8A-8H, can be displayed. User 301 has visual contact 303 with the visual-tasks displayed on display screen 313 and has an input capability 305 for responding to device 311 according to perceptions of the displayed patterns and to queries presented via device 311. Non-limiting examples of device 311 include interactive computing devices such as tablet computers; smartphones; and personal computing devices. Target visual patterns are displayed visually on display screen 313. In certain embodiments of the invention, interactive queries presented to user 301 on device 311 are also presented via display screen 313. In other embodiments, interactive queries are presented to user 301 via other output facilities of device 311, such as via audio. Likewise, in various embodiments, interactive responses of user 301 are input into device 311 via display screen 313 using touch-screen properties. According to various embodiments, the user's device 311 comprises at least one of (not shown): the at least one processor, the input interface device, and the audio device, which are not shown.

In certain embodiments of the present invention, user device 311 is a device that connects to a remote processor 321. In a related embodiment, processor 321 is equipped with non-transitory memory storage 327 for persistent storage of program instructions and data. In a related embodiment, processor 321 and non-transitory storage 327 are contained within a server 323. Processor 321 connects to user device 311 via a communication link 325. In various embodiments, communication link 325 is a virtual link. In a related embodiment, communication link 325 is realized by a wireless link 315 from device 311 to a network 317, such as the Internet, and by a link 319 from processor 321 to network 317.

According to embodiments of the present invention, a dataset 331 is prepared in advance by associating a plurality of visual-tasks threshold measurements with direct measures of at least one vision related physical condition, as statistically computed for a large number of subjects. In related embodiments, by using dataset 331, it is possible to determine at least one vision related physical condition of a user by measuring the user's response to at least two different visual-tasks and then looking up the corresponding measurement thresholds in dataset 331 in order to determine or rule out at least one vision related physical condition.

In other embodiments of the invention, processor 321 is contained within device 311. In related embodiments, dataset 331 is also contained within device 311, and non-transitory storage 327 is further contained within device 311.

In an embodiment of the invention, an application 341 runs on processor 321. In another embodiment, the application 341 runs on device 311. In still another embodiment, the application 341 is distributed between device 311 and processor 321.

The application 341 controls the display of visual-tasks on display screen 313, coordinates interactive responses from user 301, stores and retrieves interim data 343, accesses dataset 331 to determine a measure of at least one vision related physical condition from at least two different visual-tasks, detects zero or more visual deficiencies and/or conditions, and prepares report 345 for presentation.

Figure 4:
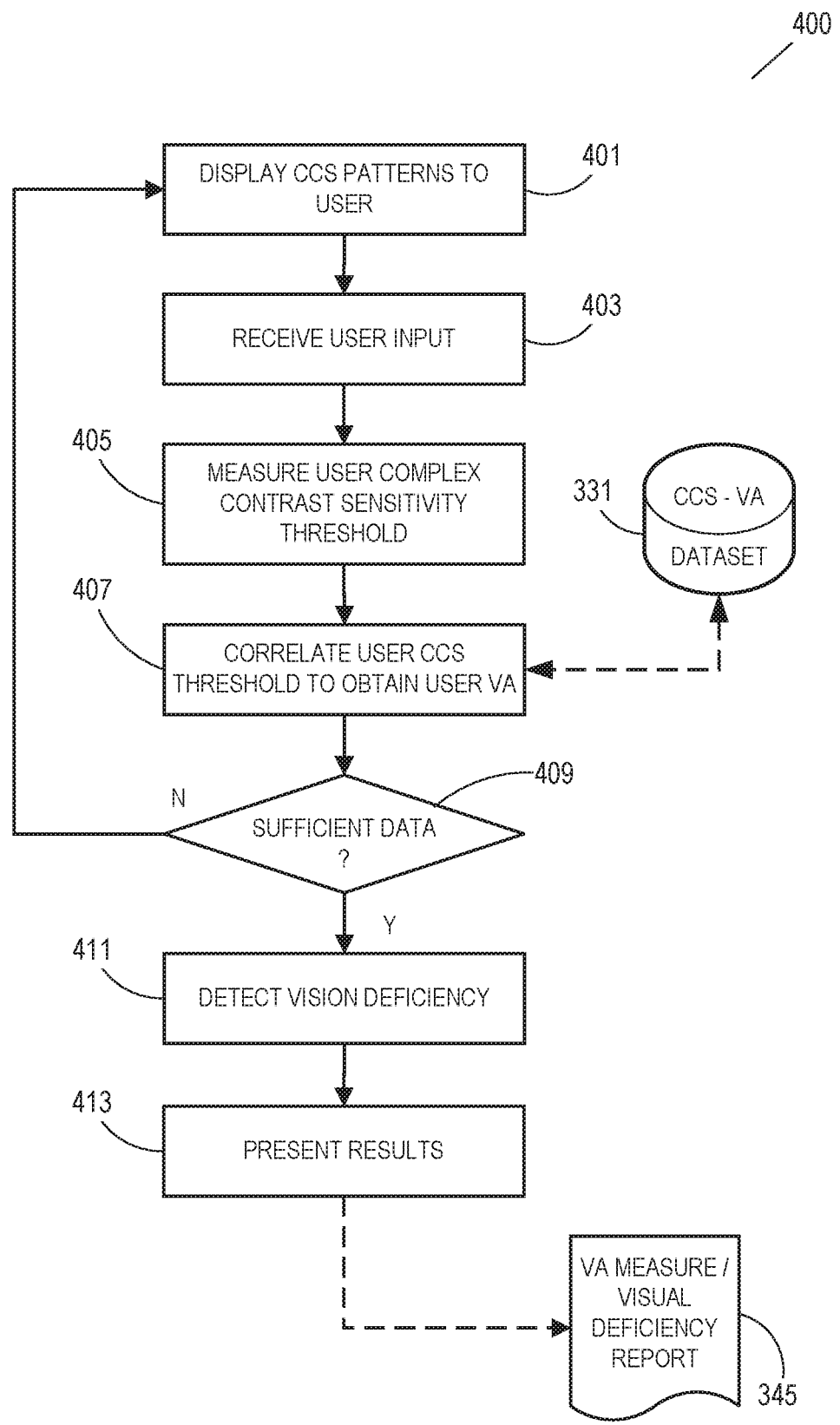
FIG. 4 is a flowchart of a method for determining at least one vision related physical condition from at least two visual tasks and a predetermined combination of their corresponding threshold measurement, according to another embodiment of the present invention.

FIG. 4 is a flowchart of a method 400 for determining at least one vision related physical condition from at least two visual-tasks, according to another embodiment of the present invention. In a step 401, at least two visual-tasks are displayed to user 301 (FIG. 3). In a step 403, input is received from user 301, as previously described, indicating the corresponding related thresholds. In a step 405 user 301 corresponding thresholds are measured interactively, by displaying at least two selected visual-tasks to user 301 and receiving responses from user 301 according to user 301's perception and physical condition.

In a step 407, the measurements of user's 301 corresponding thresholds are correlated with dataset 331. At a decision point 409 it is checked whether or not there is sufficient data to determine a measure of visually related condition. If there is sufficient data, in a step 411 a visual deficiency and/or condition, if any, is detected, and in a step 413 results 345 are output, including the measure of the condition and identification of visual deficiencies and/or condition, if any. If there is not yet sufficient data, then step 401 is repeated as needed to obtain sufficient data.

An additional embodiment of the present invention provides an application for a data processing device (such as processor 321 and/or user device 311, including, but not limited to a smartphone, a tablet computer, or a personal computer) containing machine-readable executable program code stored in non-transitory storage 327, which, when executed by the data processing device causes the data processing device to perform a method of the present invention, including, but not limited to method 400 as shown in FIG. 4 and described above.

Therefore, an embodiment of the present invention discloses a new method for presenting images to a user, for determining at least one vision related physical condition, the method comprising processor implemented steps of:
  displaying two or more visual-tasks selected from the group essentially consisting of:
    CS target pattern,
    CCS,
    backward masking with any of: CS target pattern, CS central target pattern with flanking patterns, tumbling target symbol, and the tumbling central target symbol between plurality of flanking symbols, and and any combination thereof;
  measuring responses of the user to the displayed visual-tasks;
  associating the user's responses with a dataset of expected results, respective to the displayed the visual-tasks; and
  retrieving measurements of least one vision related physical condition, corresponding to a predetermined combination of the degree of correlation between the user's responses and the associated expected results.

According to another embodiment, the present invention discloses a new method for presenting images to a user, for determining at least one vision related physical condition, the method comprising processor implemented steps of:
  displaying two or more visual-tasks to a user, wherein at least one of the visual-tasks is configured for complex contrast sensitivity (CCS) examination, via a display device;
  measuring responses of the user to the displayed visual-tasks, via a input interface;

associating the user's responses with a dataset of expected results, respective to the displayed visual-tasks; and retrieving measurements of least one vision related physical condition, corresponding to a predetermined combination of the degree of correlation between the user's responses and the associated expected results According to another embodiment, the present invention discloses a new transitory or non-transitory computer readable medium (CRM) comprising executable code instructions, which instructions when executed by a data processor cause the data processor to perform a method for presenting images to a user, for determining at least one vision related physical condition, the method comprising steps of:

displaying two or more visual-tasks to a user, wherein at least one of the visual-tasks is complex contrast sensitivity (CCS) examination;

measuring responses of the user to the displayed visual-tasks;

associating the user's responses with a dataset of expected results, respective to the displayed the visual-tasks; and retrieving measurements of least one vision related physical condition, corresponding to a predetermined combination of the degree of correlation between the user's responses and the associated expected results.

According to another embodiment, the present invention discloses a new device configured to determine at least one vision related physical condition of a user, the device comprising:

at least one display-device, configured to display at least two visual-tasks to the user, wherein at least one of the visual-tasks is configured to examine complex contrast sensitivity (CCS);

at least one input-device, configured to collect and interpret, user's response/s to the displayed visual-tasks; and at least one processor configured to:
associate the user's responses with a dataset of expected results, respective to the displayed the visual-tasks; and
retrieve measurements of least one vision related physical condition, corresponding to a predetermined combination of the degree of correlation between the user's responses and the associated expected results.

According to some embodiments, the display device is at least one selected from: a handheld video game device, a computer screen, a television screen, a smart phone, a tablet computer, a projector, a hologram projector, and any device that can display the images to a user.

According to some embodiments, the input-device is configured to perform at least one of:
collect tactile- and/or touch-input of the user;
recognize voice responses of the user;
monitor and observe the user for at least one of: gesture, eye-movements, blinks and brain waves.

According to some embodiments, the display-device, is configured to provide the user with visual-instructions in regards to a required responses and/or visual-feedback in regards to the received responses.

According to some embodiments, the device further comprises an audio-device, configured to provide the user with audio-instructions in regards to a required response and/or audio-feedback in regards to the collected response.

According to some embodiments, the visual-tasks are prepared and stored by a remote server and sent to display-device via a network.

According to some embodiments, the user's responses and/or assignment is stored in the dataset in a remote server via a network.

According to some embodiments, the display-device is configured for displaying for one of the user's eyes or for both.

According to some embodiments, at least one of the visual-tasks comprises at least one feature from the group consisting of:
contrast sensitivity (CS) target pattern;
backward masking with any of: CS target pattern, the CS central target pattern with flanking patterns, tumbling target symbol, and tumbling central target symbol between plurality of flanking symbols;
CCS examination; and
any combination thereof.

According to some embodiments, the visual task of CCS examination comprises at least one of:
CS central target pattern with flanking patterns having predetermined spacing distance there-between,
tumbling target symbol with flanking patterns having predetermined spacing distance there-between, and
tumbling central target symbol between plurality of flanking symbols having predetermined spacing distance there-between.

According to some embodiments, the physical condition is at least of the group consisting of: Astigmatism, Presbyopia, Amblyopia, Diabetic Retinopathy, Glaucoma, Age-Related Macular Degeneration (AMD), Major Depression, Dyslexia, attention deficit disorder (ADD), attention deficit hyperactivity disorder (ADHD).

According to some embodiments, the at least two visual-tasks are at least two CS target pattern, having at least one different character selected from the group consisting of: size of the target pattern, orientation of the target pattern, color of the target pattern, exposure duration, exposure spatial frequency, and exposure spatial phase.

According to some embodiments, the at least two visual-tasks are at least two CS central target pattern, having at least one different character selected from the group consisting of: the predetermined spacing, size of the target pattern, orientation of the target pattern, color of the target pattern, exposure duration, exposure spatial frequency, and exposure spatial phase.

According to some embodiments, the at least two visual-tasks are at least two tumbling target symbol, having at least one different character selected from the group consisting of: size of the target symbol, orientation of the target symbol, color of the target symbol, exposure duration, exposure spatial frequency, and exposure spatial phase.

The method of claim 1, the at least two visual-tasks are at least two tumbling central target symbol with plurality of flanking symbols, having at least one different character selected from the group consisting of: size of the flanking symbols, orientation of the target symbol, orientation of the flanking symbols, color of the target symbol, color of the flanking symbols, exposure duration, exposure spatial frequency, exposure spatial phase, the spacing distance between the flanking symbol and the target symbol, and the spacing distance between the flanking symbols there-between.

According to some embodiments, the visual related condition of the user is determined with and/or without optical correction of the user's vision.

According to some embodiments, the method further comprising reporting the retrieved measurements of the at least one visual related physical condition.

According to some embodiments, the spacing distance between the tumbling central target symbol and the flanking symbols is between 0.01% and 150% of the symbol size.

According to some embodiments, the displaying comprises repetitions for each of the displayed visual-tasks.

According to some embodiments, the dataset of the expected results comprises responses of users with normal vision and/or responses of users which are diagnosed for having at least one vision related physical condition.

According to some embodiments, the method further comprising providing to the user visual and/or audio instructions in regards to a required response.

According to some embodiments, the method further comprising providing to the user visual and/or audio feedback in regards to the received responses.

According to some embodiments, the measuring comprises at least one of:
  collecting the user's response via a tactile and/or touch input device;
  recognizing voice of the user;
  monitoring and observing the user for at least one of: gesture, eye-movements, blinking, and brain waves.

According to some embodiments, the displaying is configured for one of the user's eyes or for both.

According to some embodiments, the at least two visual-tasks comprise at least one of: dynamic-images, static-images, and any combination thereof.

According to some embodiments, wherein the measuring comprises:
  classifying the user's response as being correct vs. incorrect; or
  classifying the user's response for its' level of correctness.

According to some embodiments, the retrieving measurements of least one vision related physical condition, is further responsive a predetermined threshold for the degree of correlation.

Figure 5A:
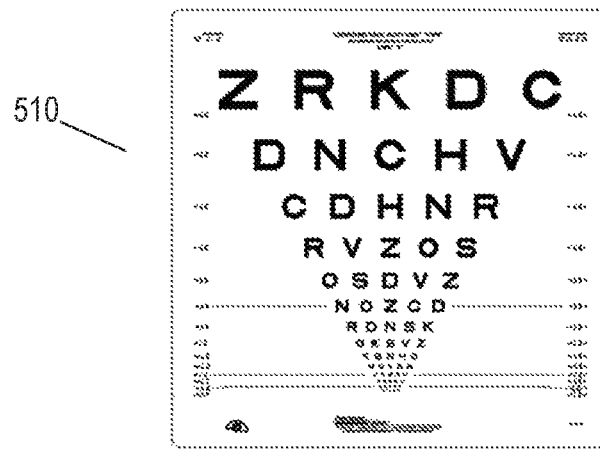
FIGS. 5A, 5B and 5C conceptually illustrate ETDRS chart, tumbling E chart, and backward masking chart, respectively.
Figure 5B:
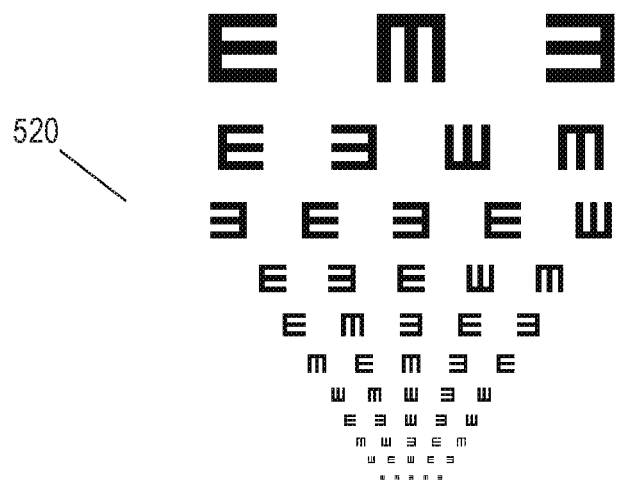
Figure 5C:
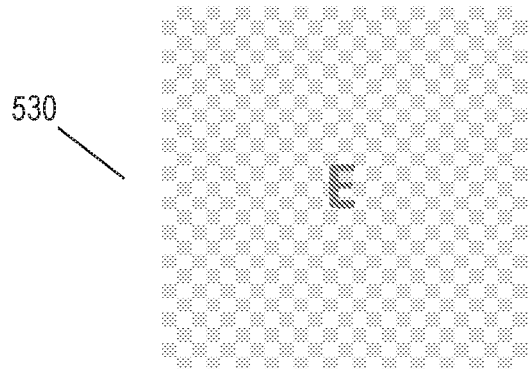

FIGS. 5A, 5B and 5C conceptually illustrate ETDRS chart 510, tumbling E chart 520, and backward masking test 530, respectively. Where the backward masking comprises two phases: exposure of the target symbol 531 (for example the number "2") and then exposure of a mask 532. The target and mask can be the same, as long as at least one character is changed, for a non-limiting example: color, orientation, dimensions, intensity, with a twist, with background, letters, Gabor and more.

Figure 6A:
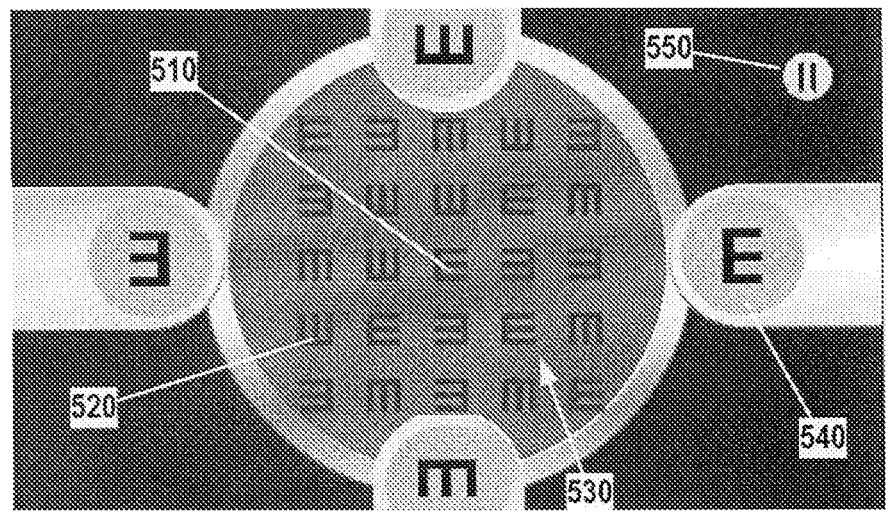
Figure 6B:
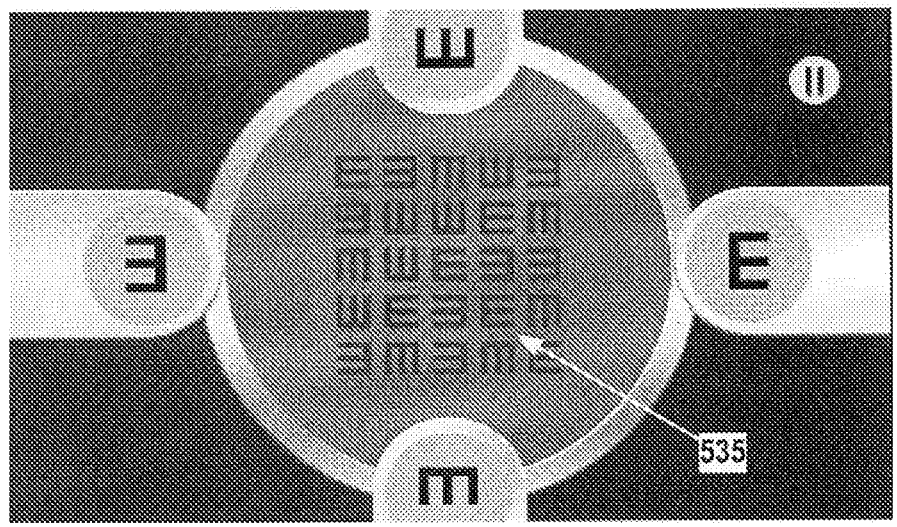

FIGS. 6A and 6B conceptually illustrate the visual task of tumbling central target 610 symbol between plurality of flanking symbols 620, presenting two different predetermined spacing distance there-between 630,635; FIG. 6A demonstrates a spacing between the symbols which equals to the target symbol dimensions (denoted as 1.0), where FIG. 6B demonstrates a spacing of 40% (denoted as 0.4) of the target's dimensions. During the task the user is requested to select the corresponding button 640, showing the correct direction of the central target 610.

Figure 7:
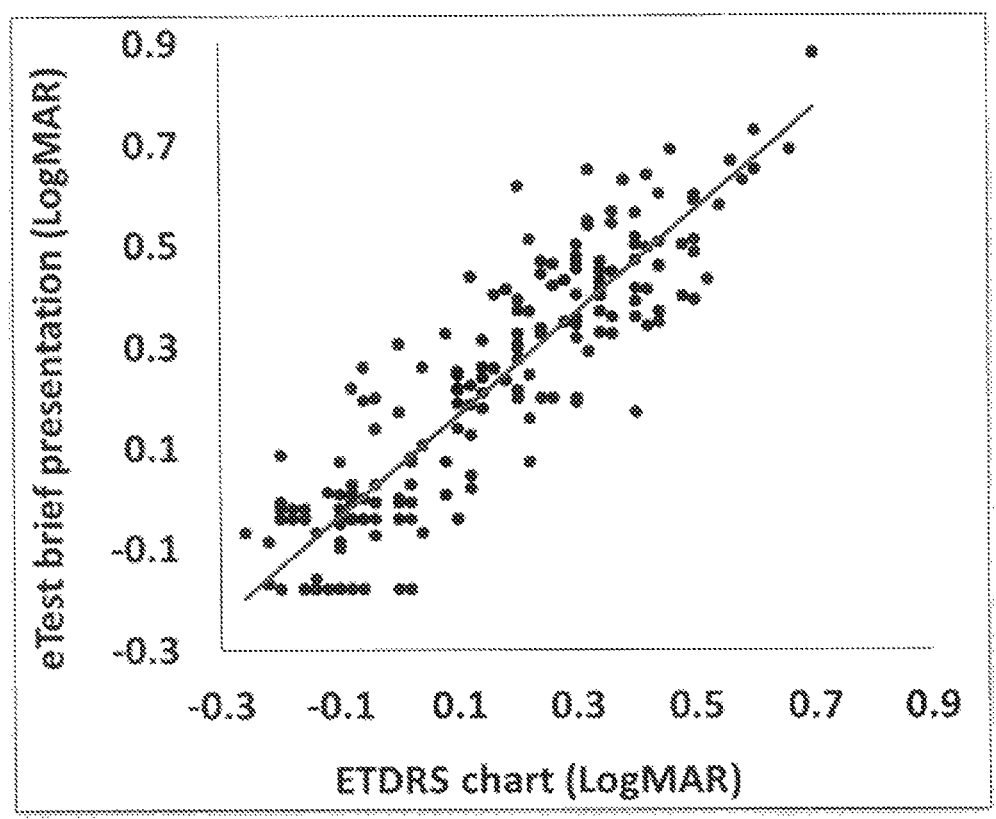
FIG. 7 conceptually illustrates the correlation of between ETDRS chart and E-Test.

FIG. 7 illustrates the correlation of between ETDRS chart and E-Test. It is demonstrated that the correlation found is about 90%.

FIGS. 8A-8H conceptually illustrate few more non limiting examples for visual-tasks presented to the user, including Gabor patch- or tumbling E-target patterns with flanking patterns at various arrangements:
  FIG. 8A, a central target Gabor patch, with diagonal flankers;
  FIG. 8B, a central target Gabor patch, with vertical flankers;
  FIG. 8C, a central target Gabor patch, with cross flankers;
  FIG. 8D, a central target Gabor patch, within a rectangle/square flankers;
  FIG. 8E, a central target tumbling E, with lateral flankers;
  FIG. 8F, a central target tumbling E, with vertical flankers;
  FIG. 8G, a central target tumbling E, with cross flankers; and
  FIG. 8H, a central target tumbling E, with rectangle/square flankers.

FIGS. 8A-8H demonstrate a similar orientation for the target-images and their flankers, however it should be noted that, the flankers may be presented with different orientations than of the target-image (not shown).

TESTING EXAMPLES

Figure 9A:
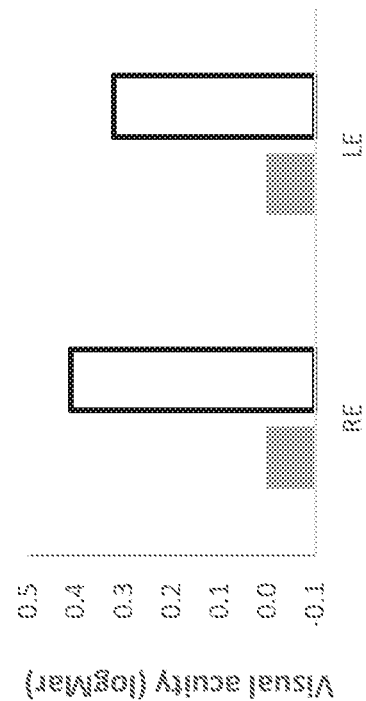
FIGS. 9A and 9B disclose testing results for the right eye (RE) and left eye (LE) of a Glaucoma patient vs. normal vision subject.
Figure 9B:
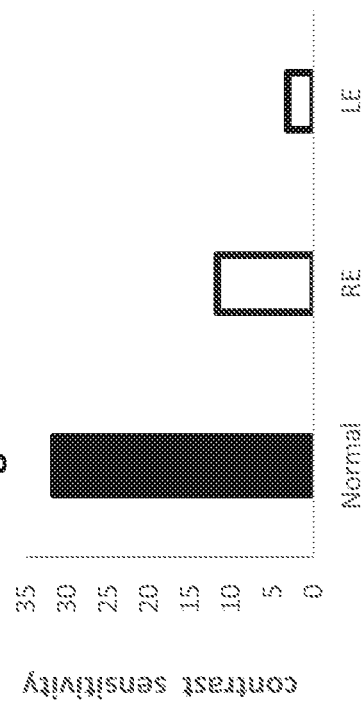

FIGS. 9A and 9B disclose testing results for the right eye (RE) and left eye (LE) of a Glaucoma tested patient vs. normal-vision tested subject. FIG. 9A demonstrates the results of CS testing (measured as 1 or 100 divided by % contrast–a threshold). The left bar shows measurements of CS of a normal subject (black bar), vs. the RE and the LE of a Glaucoma tested patient (white bars). The results show an evident for lower contrast sensitivity for Glaucoma patient.

FIG. 9B demonstrates the results of static VA testing, measured in logMar (gray bars) of a Glaucoma subject (RE,LE) as measured on static VA, vs. the white bars of the Glaucoma tested of the same patient (RE,LE) with CVA. The static VA shows normal scores for both eyes of the Glaucoma patients while the CVA shows the huge abnormality. Thus, it is evident that pure static VA testing demonstrate normal score (0 logMar, 6/6) for both RE and LE (gray bars), while CVA is demonstrating huge reduction of more than three (3) lines (over 100% reduction). Thus, using CVA is much more informative and enabling diagnostic.

FIGS. 10A-10D disclose testing results of an Amblyopia tested patient (white bars) vs. a normal vision tested subject with corrected (black bars) or non-corrected (gray bars) vision.

Figure 10B:
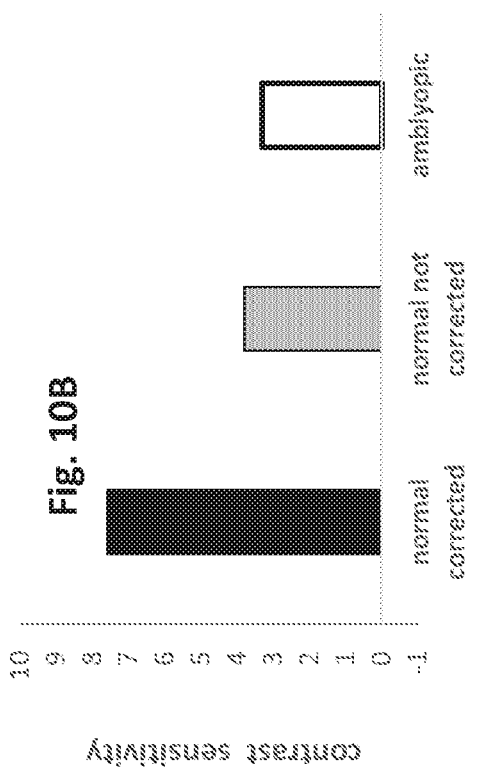
FIGS. 10A, 10B, 10C and 10D disclose testing results of an Amblyopia patient vs. normal corrected/not-corrected vision subject.
Figure 10D:
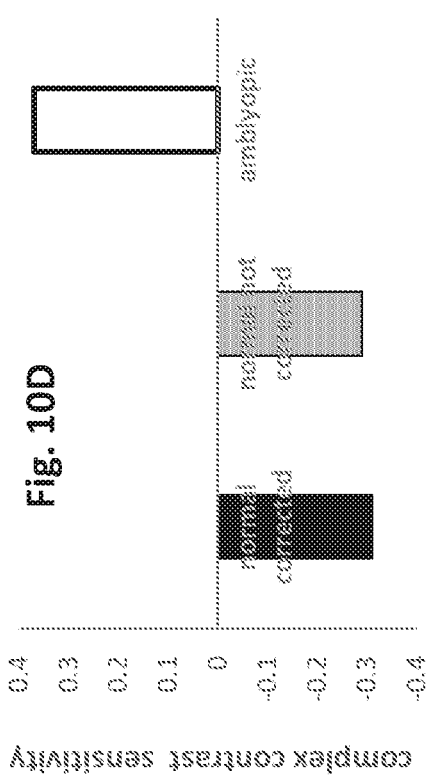
Figure 10A:
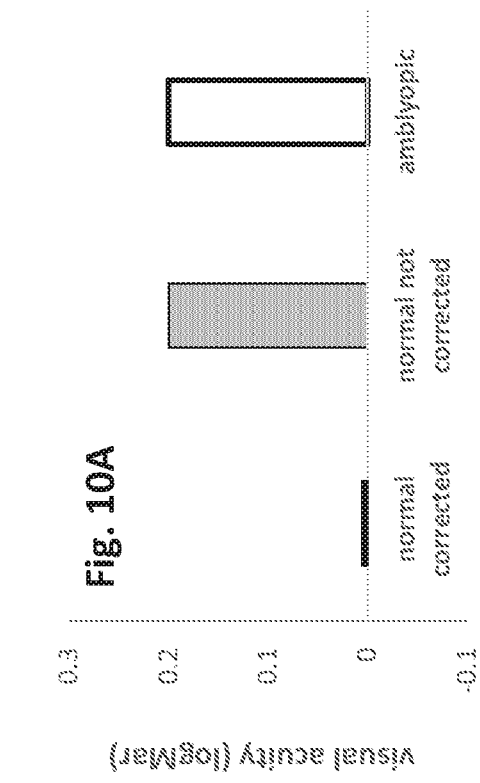

FIG. 10A demonstrates measuring of VA, measured in logMar, and it is shown that the VA of the normal eye when optically corrected (black bar) is 6/6. However, if the testing is performed with no optical correction (gray bar), there is a clear reduction of the VA, and it is very similar to the VA of the amblyopic eye (white bar). Thus, it is demonstrated that by using this VA measure one cannot distinguish between uncorrected vision and visual dysfunction such as Amblyopia. Thus, further testing should be performed.

FIG. 10B demonstrates measuring of CS. Here again it is shown that the CS testing alone cannot distinguish between uncorrected (gray bar) and Abnormal vision (white bar).

Figure 10C:
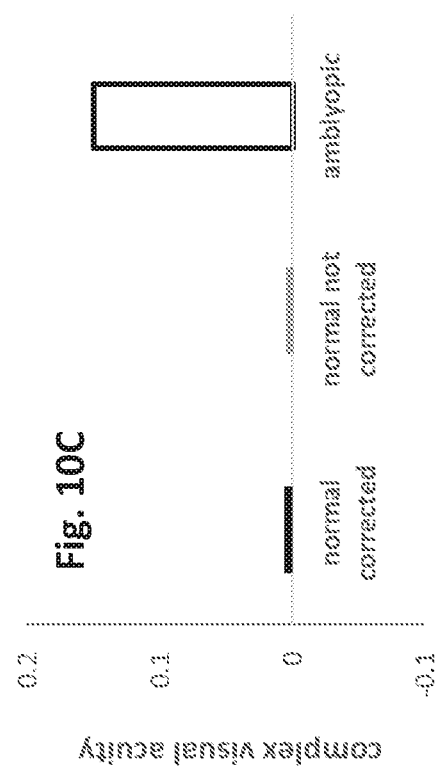

However, the testing results of CVA, as in FIG. 10C, and CCS, as in FIG. 10D, it is clearly shown that the uncorrected eye is behaving like normal eye, while the Amblyopic eye is showing a clear and remarkable difference and abnormality.

Figure 11A:
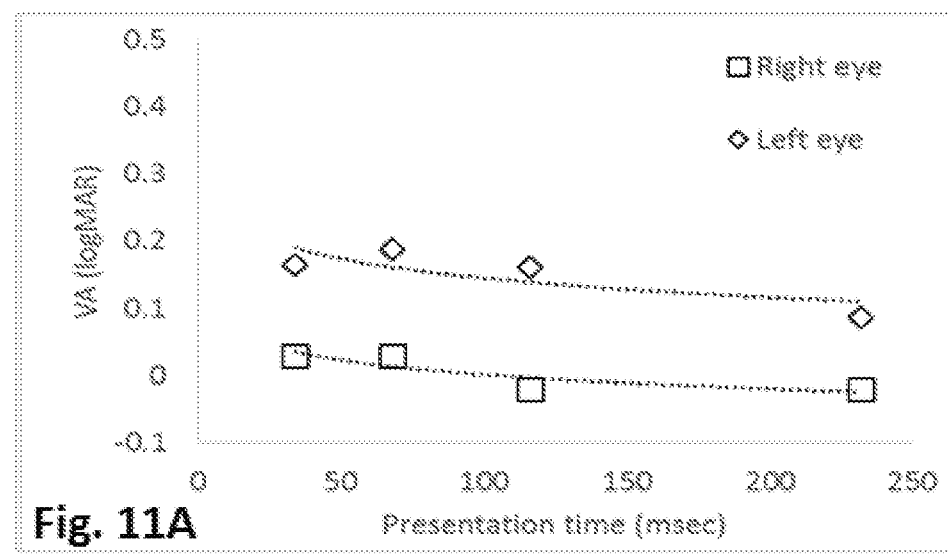
FIGS. 11A, 11B, 11C, 11D, and 11E disclose testing results of VA and CCS, of two different subjects.
Figure 11B:
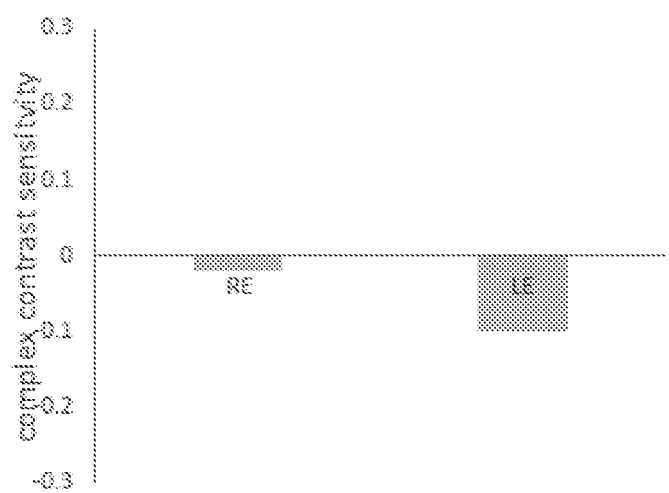
Figure 11C:
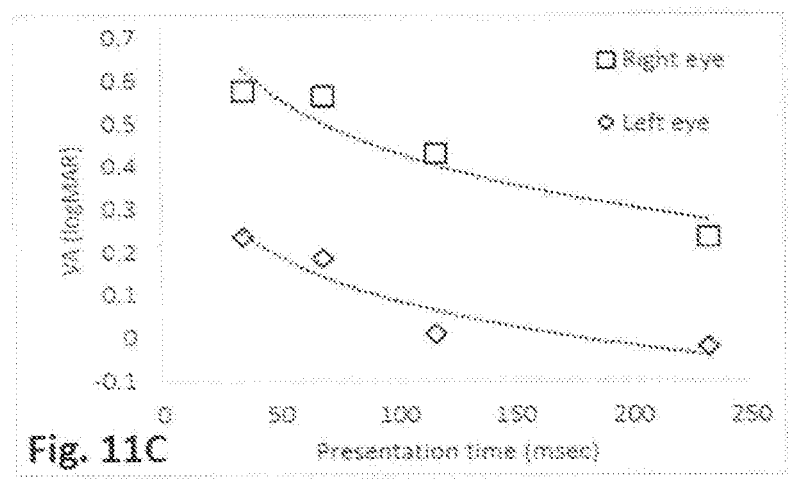
Figure 11D:
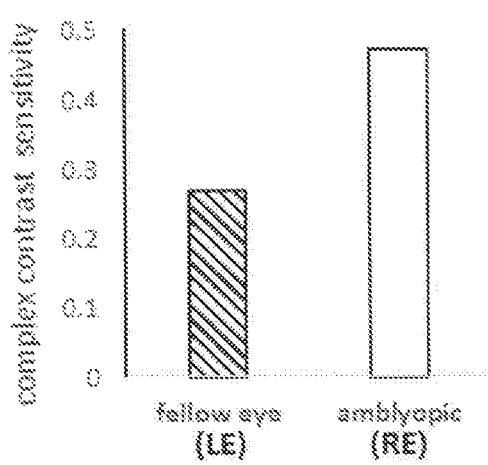
Figure 11E:
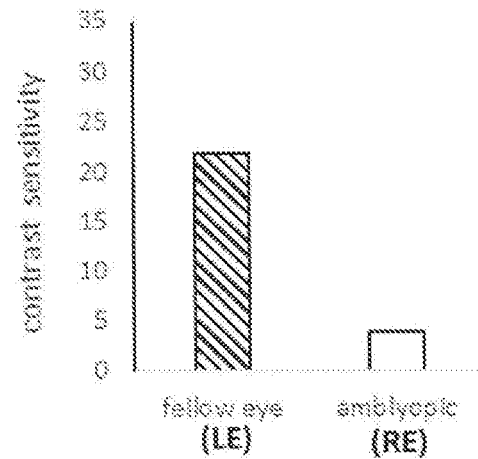
Figure 12C:
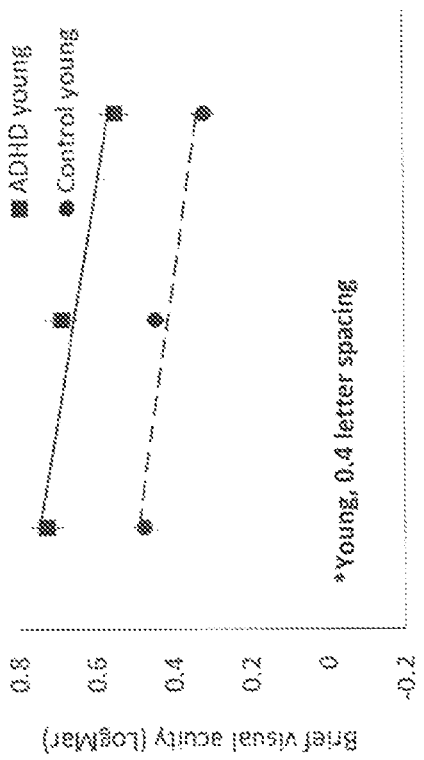
FIGS. 12A-12D illustrate testing for determining ADHD in children and adults.
Figure 12D:
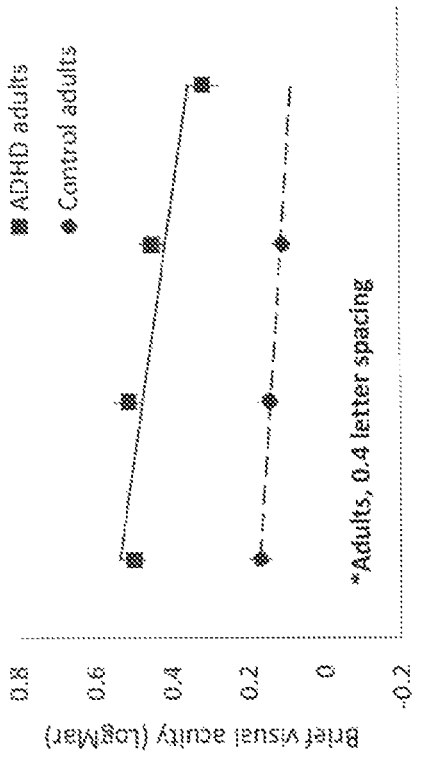
Figure 12A:
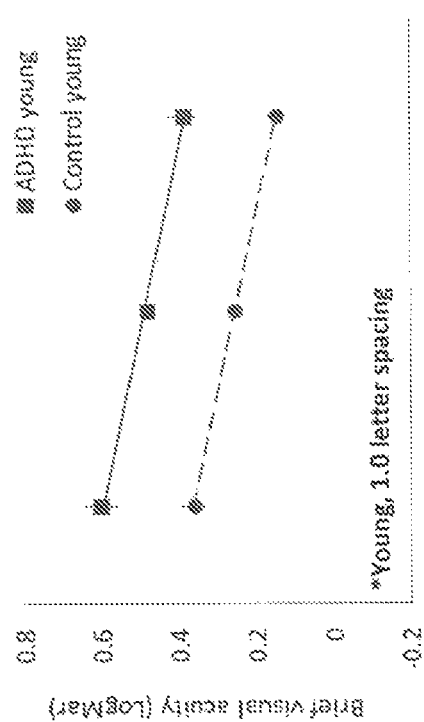
Figure 12B:
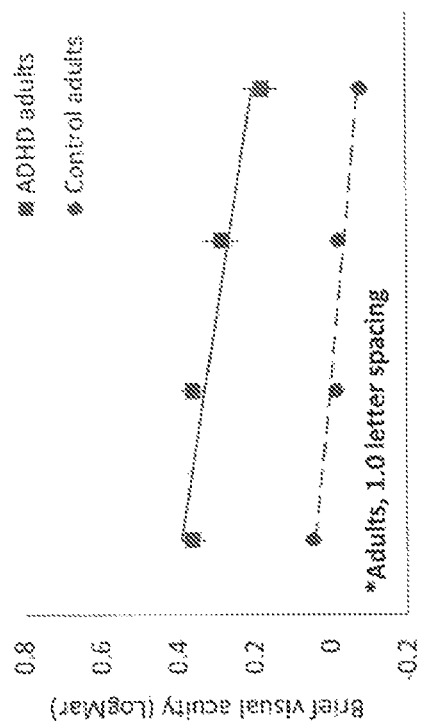

FIGS. 11A-11E disclose testing results for two subjects, FIGS. 11A and 11B of a first subject, and FIGS. 11C, 11D and 11E of a second subject. FIGS. 11A and 11C demonstrate results of the two subjects tested for VA, using E letters with spacing of 1 letters, measured under various short presentation times (30 to 240 msec). The test was repeated two (2) times, under monocular conditions (right and left eyes were tested separately). The Y axis represents the VA threshold in logMAR; the X axis represents the presentation time of the stimulus in msec. The squared graphs represent results of the right eye and the diamond graphs represent results of the left eye. As in FIGS. 11A and 11C both subjects show difference between the two eyes, while one eye shows more abnormal pattern of results, than the other.

However, when testing both subjects with CCS test, the results of the first subject, as in FIG. 11B, do not demonstrate suppression (above 0) in either of the eyes; the results of the first subject demonstrate normal or almost normal pattern of modulation. Therefore the first subject is detected as having ocular hyper-tension with a risk to glaucoma.

The CCS results of the second subject, as in FIG. 11D, demonstrate abnormal CCS in both eyes, while one eye demonstrates a much worse result than the other. This pattern is typical to subjects with Amblyopia, most likely with Strabismus. Therefore, when testing the second subject for CS, the results, as in FIG. 11E, reveal that one eye (the right eye) is an Amblyopic eye and the other eye (the left eye) is the fellow eye.

Thus, the results of FIGS. 11A-11E demonstrate that at least two different tests are required, to distinguish between suspected eye conditions that might show similar pattern of results in one method, but can be separated using CCS.

EXAMPLES FOR DETERMINING ADHD

FIGS. 12A, 12B, 12C and 12D illustrate testing for determining ADHD in children and adults, as shown in the following examples.

In the following examples a paradigm based on spatial and temporal stimulation is used to identify ADHD symptoms, both in young and adult participants.

Each of the participant's VA was examined by an optometrist in order to make sure the results are not confounded by poor VA. In addition, the group of young participants that was previously diagnosed with ADHD and the age-matched control group are tested for normal VA using a single "E" shape target using the E-Test (see below) in order to rule out poor VA. All of the participants had VA of 0.1 logMar or better at near distance (15").

The Participants:
Adult diagnosed ADHD, all are self-reported as diagnosed ADHD by specialist, Number of participants: 28 (14 males); Age average SD: 25.6±10.4 SD
Adult control group, Number of participants: 17 (8 males); Age average: SD 25.2±3 SD.
Young diagnosed ADHD, all reported by their parents as diagnosed as ADHD by a clinician, Number of participants: 21; Age average 9.3±2.7 SD.
Young control participants, Number of participants: 43 (23 males); Age average 9.5±4 SD.

The E-Test with crowding symbols: Measurements were made using a prototype dynamic digital assessment tool, developed by GlassesOff™, on smartphones, previously shown to reliably measure functional near VA, and were compared between diagnosed-ADHD and control groups. The test can be performed on any kind of screen (mobile or PC). Here are presented testing results on mobile device screens:

Testing distance of 15";
Stimuli:
E-shape target embedded within a 5×5 matrix of similar E-shapes, with a randomly chosen orientation: Up, Down, Left and Right.
Two spacing distances: 0.4 and 1 letter, producing crowding.
Presentation duration: between 30 to 240 milliseconds (msec).
The task: to detect the orientation of the central E-shape (i.e., the target) namely "Random E's", this involves the patient identifying the direction that the letter "E" is facing. Looking at the letter on a chart or projection, the patient points either up, down, to the left, or to the right, depending on the direction that the letter is facing.

A minimal detectable target size for each combination of presentation duration and spacing distance was measured in a separate lock, using the adaptive ("staircase") method.

RESULTS: FIGS. 12A-12D demonstrate that Despite normal VA on the clinical static ETDRS chart, the test showed a large and significant reduction in visual performance in ADHD subjects compared to control subjects, in both age groups and for all presentation times and spacing distances.

CONCLUSIONS: a self-administered dynamic digital tool that can be used for objective assessment of ADHD symptoms and can constitute an objective screening tool to assist clinical diagnosis of ADHD. This tool ensures the results are not confounded by poor VA by confirming intact VA in the single letter target testing block. This tool is very easy to operate and can be used practically anywhere by anyone. Under-development of visual functions, which normally characterizes vision in young children, persists in adults with ADHD symptoms and becomes apparent under spatial and temporal load conditions.

It is understood that various other modifications will be readily apparent to those skilled in the art without departing from the scope and spirit of the invention. Accordingly, it is not intended that the scope of the claims appended hereto be limited to the description set forth herein, but rather that the claims be construed as encompassing all the features of the patentable novelty that reside in the present invention, including all features that would be treated as equivalents thereof by those skilled in the art to which this invention pertains.

What is claimed is:

1. A method for presenting images to a user, for determining at least one vision related physical condition, the method comprising processor implemented steps of:
displaying two or more visual-tasks to a user, wherein:
at least one of the visual-tasks is configured for complex contrast sensitivity (CCS) examination, which is comprising a target contrast sensitivity (CS) pattern in the presence of flanking patterns, and
at least one of the visual-tasks consists a single CS pattern, which is similar in shape to the target CS pattern of the CCS examination;
measuring responses of the user to the displayed visual-tasks;
comparing between the responses of the user to the visual-tasks having e similar target CS pattern;
associating and comparing the user's responses and their relation with a dataset of expected results, respective to the displayed visual-tasks; and
retrieving measurements of least one vision related physical condition, corresponding to a predetermined combination of the degree of correlation between the user's responses and the associated expected results.

2. The method of claim 1, further comprises selecting at least one visual-task, which comprises at least one feature of the group consisting of:
contrast sensitivity (CS) target pattern;
backward masking with any of: CS target pattern, the CS central target pattern with flanking patterns, tumbling target symbol, and tumbling central target symbol between plurality of flanking symbols;

CCS examination; and any combination thereof.

3. The method of claim 2, wherein the visual task of CCS examination comprises at least one of:

CS central target pattern with flanking patterns having predetermined spacing distance there-between, tumbling target symbol with flanking patterns having predetermined spacing distance there-between, and tumbling central target symbol between plurality of flanking symbols having predetermined spacing distance there-between.

4. The method of claim 1, wherein at least one of the following holds true:

the physical condition is at least of the group consisting of: Astigmatism, Presbyopia, Amblyopia, Diabetic Retinopathy, Glaucoma, Age-Related Macular Degeneration (AMD), Major Depression, Dyslexia, attention deficit disorder (ADD), attention deficit hyperactivity disorder (ADHD);

the visual related condition of the user is determined with and/or without optical correction of the user's vision;

the method further comprises reporting the retrieved measurements of the at least one visual related physical condition;

the displaying comprises repetitions for each of the displayed visual-tasks;

the method further comprising providing to the user visual and/or audio instructions in regards to a required response;

the method further comprising providing to the user visual and/or audio feedback in regards to the received responses;

the displaying is configured for one of the user's eyes or for both;

the at least two visual-tasks comprise at least one of: dynamic-images, static-images, and any combination thereof; and the measuring comprises classifying the user's response as being correct vs. incorrect, or classifying the user's response for its' level of correctness.

5. The method of claim 1, wherein the at least two visual-tasks are which are configured by the similar shape target CS pattern, comprise at least one different character for the similar target patterns, the character is at least one selected from the group consisting of: size of the target pattern, orientation of the target pattern, color of the target pattern, exposure duration, exposure spatial frequency, and exposure spatial phase.

6. The method of claim 1, wherein the at least two visual-tasks are at least two CS central target pattern, having at least one different character selected from the group consisting of: the predetermined spacing, size of the target pattern, orientation of the target pattern, color of the target pattern, exposure duration, exposure spatial frequency, and exposure spatial phase.

7. The method of claim 1, wherein the at least two visual tasks are at least two tumbling target symbol, having at least one different character selected from the group consisting of: size of the target symbol, orientation of the target symbol, color of the target symbol, exposure duration, exposure spatial frequency, and exposure spatial phase.

8. The method of claim 1, wherein the at least two visual-tasks are at least two tumbling central target symbol with plurality of flanking symbols, having at least one different character selected from the group consisting of: size of the flanking symbols, orientation of the target symbol, orientation of the flanking symbols, color of the target symbol, color of the flanking symbols, exposure duration, exposure spatial frequency, exposure spatial phase, the spacing distance between the flanking symbol and the target symbol, and the spacing distance between the flanking symbols there-between.

9. The method of claim 2, wherein the spacing distance between the tumbling central target symbol and the flanking symbols is between 0.01% and 150% of the symbol size.

10. The method of claim 1, wherein the dataset of the expected results comprises responses of users with normal vision and/or responses of users which are diagnosed for having at least one vision related physical condition.

11. The method of claim 1, wherein the measuring comprises at least one of:

collecting the user's response via a tactile and/or touch input device;

recognizing voice of the user;

monitoring and observing the user for at least one of: gesture, eye-movements, blinking, and brain waves.

12. The method of claim 1, wherein the step of retrieving measurements of at least one vision related physical condition, is further responsive to a predetermined threshold for the degree of correlation.

13. The method of claim 1, wherein the flanking patterns of the CCS examination are similar in shape to the target CS pattern.

14. The method of claim 13, wherein the flanking patterns which are similar in shape to the target CS pattern, comprise at least one different character selected from the group consisting of: size of the target pattern, orientation of the target pattern, color of the target pattern, exposure duration, exposure spatial frequency, and exposure spatial phase.

* * * * *